United States Patent
Bowman et al.

(10) Patent No.: US 9,968,421 B2
(45) Date of Patent: May 15, 2018

(54) TOOTH POSITIONER AND VIBRATOR COMBINATION

(71) Applicant: OrthoAccel Technologies, Inc., Bellaire, TX (US)

(72) Inventors: Steven J. Bowman, Bellaire, TX (US); Michael K. Lowe, Bellaire, TX (US)

(73) Assignee: OrthoAccel Technologies, Inc., Bellaire, TX (US)

( * ) Notice: Subject to any disclaimer, the term of this patent is extended or adjusted under 35 U.S.C. 154(b) by 790 days.

(21) Appl. No.: 13/850,151

(22) Filed: Mar. 25, 2013

(65) Prior Publication Data

US 2013/0252193 A1  Sep. 26, 2013

Related U.S. Application Data

(60) Provisional application No. 61/615,480, filed on Mar. 26, 2012.

(51) Int. Cl.
| | | |
|---|---|---|
| *A61C 3/00* | (2006.01) | |
| *A61C 7/00* | (2006.01) | |
| *A61C 7/08* | (2006.01) | |

(52) U.S. Cl.
CPC .............. *A61C 7/008* (2013.01); *A61C 7/08* (2013.01)

(58) Field of Classification Search
CPC .............. A61C 7/008; A61C 7/08; A61C 7/00
USPC ...... 433/2, 6, 8, 9, 24, 29, 215, 82, 86, 118, 433/119
See application file for complete search history.

(56) References Cited

U.S. PATENT DOCUMENTS

| | | | |
|---|---|---|---|
| 3,407,500 A | 10/1968 | Kesling | |
| 4,123,844 A | 11/1978 | Kurz | |
| 4,229,165 A | 10/1980 | Kurz | |
| 4,244,688 A | 1/1981 | Kurz | |
| 4,348,177 A | 9/1982 | Kurz | |
| 4,348,178 A | 9/1982 | Kurz | |
| 4,382,780 A | 5/1983 | Kurz | |
| 4,559,013 A * | 12/1985 | Amstutz et al. | 433/22 |
| 4,898,535 A | 2/1990 | Bergersen | |
| 5,030,098 A | 7/1991 | Branford | |
| 5,554,971 A | 9/1996 | Foster | |
| 5,780,958 A | 7/1998 | Strugach | |
| 5,967,784 A * | 10/1999 | Powers | 433/229 |
| 6,450,167 B1 * | 9/2002 | David et al. | 128/848 |
| 6,632,088 B2 | 10/2003 | Voudouris | |
| 6,684,639 B2 | 2/2004 | Ichinose | |

(Continued)

FOREIGN PATENT DOCUMENTS

| | | |
|---|---|---|
| WO | WO0178217 | 10/2001 |
| WO | WO2007116654 | 10/2007 |

*Primary Examiner* — Cris L Rodriguez
*Assistant Examiner* — Mirayda A Aponte
(74) *Attorney, Agent, or Firm* — Boulware & Valoir (57) ABSTRACT

A tooth positioner is combined with a vibrational source, thus speeding orthodontic remodeling. In more detail, the device includes a tooth positioner shaped to closely fit a patient's dentition and apply a straightening force to at least one of said patient's teeth, the tooth positioner contacting labial, lingual and occlusal surfaces of said patient's dentition, the tooth positioner operably connected to a housing enclosing a power source operably connected to a vibratory source, the vibratory source being able to vibrate, thus vibrating the tooth positioner. Methods of using the positioner-vibrator combination are also disclosed.

17 Claims, 9 Drawing Sheets

(56) References Cited

U.S. PATENT DOCUMENTS

| | | | |
|---|---|---|---|
| 6,832,912 B2 | 12/2004 | Mao | |
| 7,029,276 B2 | 4/2006 | Mao | |
| 7,511,454 B1 | 3/2009 | Legg | |
| 7,712,468 B2 * | 5/2010 | Hargadon | 128/848 |
| 7,861,722 B2 * | 1/2011 | Keropian | 128/848 |
| 8,123,520 B2 | 2/2012 | Adachi | |
| 8,152,521 B2 | 4/2012 | Yamamoto | |
| 8,500,446 B2 * | 8/2013 | Lowe | 433/18 |
| 8,636,506 B2 * | 1/2014 | Pavlin | 433/6 |
| 2006/0115785 A1 * | 6/2006 | Li et al. | 433/80 |
| 2006/0223022 A1 | 10/2006 | Solomon | |
| 2006/0287620 A1 | 12/2006 | Tseng | |
| 2007/0103016 A1 | 5/2007 | Park | |
| 2007/0161461 A1 | 7/2007 | Nguyen | |
| 2007/0161931 A1 | 7/2007 | Kunita | |
| 2007/0179414 A1 | 8/2007 | Imboden | |
| 2007/0208284 A1 | 9/2007 | Huang | |
| 2007/0255188 A1 | 11/2007 | Tseng | |
| 2007/0299372 A1 | 12/2007 | Chang | |
| 2008/0129130 A1 | 6/2008 | Mun | |
| 2008/0227046 A1 | 9/2008 | Lowe | |
| 2009/0029310 A1 * | 1/2009 | Pumphrey et al. | 433/24 |
| 2009/0051312 A1 | 2/2009 | Simon | |
| 2009/0068612 A1 | 3/2009 | Wahab | |
| 2009/0224616 A1 | 9/2009 | An | |
| 2010/0055634 A1 * | 3/2010 | Spaulding et al. | 433/5 |
| 2010/0151407 A1 * | 6/2010 | Rizoiu et al. | 433/29 |
| 2011/0020761 A1 | 1/2011 | Kalili | |
| 2011/0039223 A1 | 2/2011 | Li | |
| 2011/0136070 A1 * | 6/2011 | Rubin et al. | 433/2 |
| 2011/0236849 A1 | 9/2011 | Pogorelsky | |
| 2012/0322018 A1 * | 12/2012 | Lowe et al. | 433/6 |

\* cited by examiner

TOOTH POSITIONER AND VIBRATOR COMBINATION

PRIOR RELATED APPLICATIONS

This application claims priority to U.S. Ser. No. 61/615,480, filed Mar. 26, 2012, and incorporated herein by reference in its entirety.

FEDERALLY SPONSORED RESEARCH STATEMENT

Not applicable.

REFERENCE TO MICROFICHE APPENDIX

Not applicable.

FIELD OF THE DISCLOSURE

This disclosure relates to vibrating devices for use in orthodontic remodeling.

BACKGROUND OF THE DISCLOSURE

Orthodontics is the dental specialty that treats malocclusion through the movement of teeth as well as control and modification of facial growth. Malocclusion is a problem in the way the upper and lower teeth fit together in biting or chewing—the word literally meaning "bad bite." The condition may also be referred to as an irregular bite, crossbite, or overbite. Malocclusion may be seen as crooked, crowded, or protruding teeth. It may affect a person's appearance, speech, and/or ability to eat.

Correcting malocclusions is usually accomplished by using a continuous mechanical force to induce bone remodeling, thereby enabling the teeth to move to a better position. In this approach, orthodontic appliances provide a continuous static force to the teeth via an archwire connected to brackets affixed to each tooth or via a removable appliance such as an aligner that fits over the dentition. As the teeth slowly move due to the force, the force is dissipated. The archwires or retainer are adjusted to add additional force and to continue the desired tooth movement. Although effective, this widely accepted approach takes an average of two years to complete.

Dental researchers have long postulated that a pulsating or otherwise non-static force might also be used to move teeth more rapidly and to ease the discomfort of traditional orthodontics. However, Mao was probably the first to prove that the use of cyclic forces could improve dental straightening in rabbits (see U.S. Pat. No. 6,684,639, U.S. Pat. No. 6,832,912, U.S. Pat. No. 7,029,276). Certain dynamic loading patterns (cycling force with rest periods) were shown by Mao to greatly increase bone formation compared to static loading. Inserting rest periods is now known to be especially efficacious as it allows mechano-sensitivity to be restored to the bone tissue. A point of diminishing returns is reached within each loading session. Therefore, a cyclic force can increase the rate of bone formation significantly.

U.S. Pat. No. 4,244,688, U.S. Pat. No. 4,348,177, and U.S. Pat. No. 4,382,780 describe devices used to vibrate the teeth during orthodontic treatment, although each uses a different means of applying a vibration. U.S. Pat. No. 4,244,688 employs a cumbersome external power source to power one to four small motors, whereas U.S. Pat. No. 4,348,177 uses pulsating fluids moved with the chewing motion of the jaw, and U.S. Pat. No. 4,382,780 uses a radio and speaker to set up a vibration. These devices are mounted on a bulky headgear that surrounds the head and are connected directly to the teeth by its intraoral portions. The devices are cumbersome, difficult to construct, expensive, and are difficult and uncomfortable to use, thus reducing patient compliance.

U.S. Pat. No. 5,030,098 by Branford describes a handheld device that simulates chewing in order to treat periodontal disease by increasing blood flow to the gums. The mouthpiece has a perforated malleable plate such that biting of the mouthpiece results in the plate adapting to the user's bite, which varies with each user. The external vibrator imparts motion to the mouthpiece and thus the user's teeth. The device, however, uses an external power source and vibrator. Further, the dental plate is brass, and is very unpleasant to bite on.

U.S. Pat. No. 5,967,784 by Powers describes a similar device to that described by Branford. It too is a hand-held tooth vibrator that is simple and has an exterior motor inside a housing that is connected to a vibrating mouthpiece portion for gripping between the teeth of the patient. The vibration is believed to alleviate discomfort by increasing blood flow.

The devices of Branford and Powers seem superficially similar to those described herein. However, there is no recognition in either patent that the vibratory device can be used for alveolar bone remodeling or more rapid tooth movement. Furthermore, the shape of the dental plate in each case is a very flat U- or Y-shaped member that is less effective for remodeling dentoalveolar bone. Additionally, the vibration is not optimized in frequency and amplitude for remodeling. All of these shortcomings reduce the effectiveness of these devices for craniofacial remodeling uses.

U.S. Pat. No. 6,632,088 describes a bracket with powered actuator mounted thereto to provide vibration, but this device is cumbersome, and thus may affect patient comfort and ultimately patient acceptance of the device. Further, the device locks to the bracket and archwire, and vibration of the tooth through the bracket is less than optimal, causing wear to the tooth enamel and causing discomfort.

WO2007116654 describes another intra-oral vibrating mouthpiece, but the mouthpiece is complex, designed to fit over the teeth and will be expensive to manufacture. Further, to the extent that this device vibrates the brackets, it suffers from the same disadvantages above.

US2008227046, owned by OrthoAccel, describes both intra-oral and extra-oral dental vibrators with processors to capture and transmit patient usage information. The bite plate in this application as specially designed to contact occlusal as well as lingual and/or buccal surfaces of the dentition, and thus is more effective than the prior art devices in conveying vibrational forces to the teeth. Further, the device has actually been tested in clinical trials and has been shown to speed orthodontic remodeling as much as 50%. Finally, the device is slim, capable of hands free operation, and optimized for force and frequency. Thus, its comfort level and compliance was also found to be high, with patients reporting that they liked the device. In fact, this device has been marketed as AcceleDent® in the United States, Canada, Australia, the United Kingdom and various other counties and has achieved remarkable commercial success since its introduction. AcceleDent® represents the first successful clinical approach to accelerate orthodontic tooth movement by modulating bone biology in a non-invasive and non-pharmacological manner. US2010055634, also by OrthoAccel, describes second generation vibrating dental devices with an improved bite plate, quieter and less variable motor, and further beneficial features.

Goals in orthodontics include the production of an ideal occlusion and beautiful smile in a timely manner for all patients. Unfortunately, these lofty aspirations are often not met, due to lack of patient cooperation (e.g., lack of elastic wear, poor oral hygiene, broken appliances, etc.) or errors that accumulate in the treatment process. Such errors might include: radiographic and tracing errors, errors in diagnosis, in bracket/band placement, limits in manufacturing tolerances of wires and brackets, inappropriate selection of mechanics, errors in mechanics, etc.

Consequently, a favorable orthodontic correction may be marred by a lack of detail in individual tooth positioning. The tooth positioner was invented in the forties by Dr. Kesling (see U.S. Pat. No. 3,407,500) to address such problems. The tooth positioner is a removable appliance that can assist in fine-tuning orthodontic results and may produce swifter completion of treatment, especially when the occlusion is nearly ideal and additional changes in wires or brackets may introduce other dilemmas or if the patient's interest and/or cooperation has run out.

There is considerable agreement that the tooth positioner is one of the finest retention devices ever invented. See e.g., Paula Allen-Noble, John Fuller, Clinical Impressions 13(1): 24-26 (2004) ("There is probably little argument that the positioner is the best finishing device invented."). Long-term compliance, however, has been problematic because the positioner is perceived as bulky and unaesthetic, and many therefore use the positioner as a finishing appliance, worn 24 hrs a day (except for eating and brushing) but for limited periods, e.g., about a week, and thereafter worn at night.

The first positioners introduced in the early 60's were made of a rubber-based material. As technology advanced, a variety of materials were offered for their unique properties to produce a blend of appliance efficacy and patient comfort. Silicone became very acceptable because of its aesthetic look (clear), resistance to heat and hypoallergenic properties, but it was plagued with inaccuracy arising from the fabrication process, making it less effective in correcting malocclusions.

Allesee Orthodontic Appliances, however, recently developed a new type of silicone positioner, using a more resilient and flexible material that will not distort from its original shape and continues to deliver the same force for an extended amount of time. This newly developed material allows the positioner to be processed directly on the diagnostic wax setup mounted on a plaster-free articulator, which permits the technician to observe and control proper compression and curing of the material, creating a more accurate positioner. In addition, a special coating is used to enhance the translucency. The ProFlex Positioner™ is slimmer, clearer and more resilient than past silicone positioners, making it more aesthetic and pleasing to patients, which encourages patient compliance.

U.S. Pat. No. 4,348,178 by Kurz describes a combined tooth positioner and vibrator. However, the vibration is provided by ultrasonic motor or hydraulic pump. Thus, the device is not optimized for tooth remodeling, having an incorrect frequency and force. Further, the device is held in place by a set of straps that fit around the head, so as to hold the device firmly in place while sleeping. While the idea behind Kurz has merit, its execution is clumsy and the device completely detracts from patient aesthetics and negates compliance efforts.

US2008227046 by OrthoAccel mentions that the vibratory device can be used with existing orthodontic devices, include the aligner known as Invisalign™. However, the device is not designed itself to be an aligner, nor are the connectors specially designed for this use.

Therefore, although orthodontic remodeling has greatly progressed over the decades, poor patient compliance continues to plague parents and orthodontists alike. All patients want and deserve to be comfortable as well as attractive during treatment, and minimizing treatment time and discomfort are important tools in increasing compliance. Thus, what is needed in the art are improved tools for speeding orthodontic remodeling and ensuring patient compliance with orthodontic treatments.

BRIEF SUMMARY OF THE DISCLOSURE

The invention more relates to a combination tooth positioner and vibrating dental device. Thus, the bite plates of e.g., US2008227046 and US2010055634, are replaced with a tooth positioner, specially made for each patient. The vibrator portion of the device speeds dental remodeling by as much as 50% and the tooth positioner portion which is custom crafted for each patient is widely recognized to be an excellent device for correcting malocclusion. The combination of the two, thus provides advantages of speed, the best aesthetics, and the best alignment tools, and thus encourages patient compliance and successful outcomes.

The tooth positioner can be made by any suitable methodology in the art or to be developed in the future. Suitable methods include those described in US20090068612, US2011236849, US2011039223, US2006223022 and the like. Thus, the positioner is generally made from an impression of a patient's teeth, but with at least one tooth position reset for better alignment. Thus, the positioner applies pressure to at least one of a patient's teeth, causing it to realign under the pressure, and the realignment process is accelerated by applying vibrational forces at least one time per day.

In addition to a tooth positioner, the product can be combined with an aligner. Aligners differ from tooth positioners mainly in the way that they are made and used, although the structure of the devices are similar. A tooth positioner is manually made with a casting wherein specific tooth positions on the casting are adjusted before molding a tooth position from the casting. Tooth positioners are also used as a finishing product for the final phase of treatment.

Aligners, by contrast, are custom made for each patient using a digital treatment plan wherein complex software predicts the movement of the teeth throughout treatment and several aligners for the entire course of treatment are digitally designed. Of course, positioners can also be made using digital technology, and this is becoming more common as labs and orthodontic offices are being equipped with 3D scanners and the like.

Both products are shaped to fit the teeth, with one or more positions being adjusted to apply pressure to one or more teeth. Therefore, for the purposes of this invention, the tooth positioner can also be digitally made in the manner of aligners, such as Invisalign.™

The vibrating portion of the dental device can be of any suitable design, including those described in US2008227046 and US2010055634, and preferably includes a processor for capturing and transmitting usage data, which provides an important tool for monitoring (and thus encouraging) patient compliance.

In order to combine the tooth positioner with a vibrational dental device, the tooth positioner must be modified to have a connector that operably and reversibly couples the tooth positioner to the vibrator. The connector should be sufficiently rigid to convey vibration to the resilient material of the tooth positioner. Some force will be dissipated by the resilient material that the tooth position is made of, and thus not transmitted to the dentition, but this can be accommodated by providing a slightly higher force.

The connector comprises two parts: 1) a plug or stem and 2) a socket or receptacle into which the stem fits, preferably in a snap fit. In a preferred embodiment, the socket is on the tooth positioner and the vibrator has the stem. Thus, the patient can wear the positioner alone at night, as well as use it with vibration 1 or more times per day, and the patient will not be bothered by a small protruding stem during the rest of the time the positioner is used without vibration.

In one embodiment, the stem has e.g., a cylindrical shaft for insertion into the socket in the tooth positioner. The shaft has e.g., a depression or groove circumnavigating its circumference, into which a circular spring inside the socket will fit. The application of a small amount of force stretches the spring slightly, allowing the device to be removed. The connector can also be asymmetric, thus preventing the user from inserting the tooth positioner upside down, although of course the tooth positioner itself will be asymmetric, fitting the teeth on only one orientation.

This above is only one example of a snap fit, and any snap fit design or cam lock (insert and twist) or other connecting means can be used. For example, the shaft could be provided with spring fitted buttons that snap into depressions inside the socket, and press fit spring pins are commercially available in a range of sizes. As another example, the stem could be composed of two or more prongs that fit into the socket as a cantilevered snap fit. As yet another example, the shaft can be square or rectangular or asymmetrical, yet still be combined with a circular spring or spring pins as described. A ball and socket snap fit could also be used, but may not be preferred as allowing movement about the ball joint.

Ideally, the socket or inner core is made of metal or a high durometer plastic (30-40 Shore D), such as high impact polystyrene, and which communicates vibrational forces from the extra-oral vibrating component to the intra-oral tooth positioner. The tooth positioner is thus formed over/around the socket.

The tooth positioner is custom made for each patient from a cast of the patient's dentition, but with any poor alignment corrected, or made via a digital treatment plan using e.g., an iOC, iTero, OrthoCad 3D or similar digital scanner. Preferably, the tooth positioner has a hard inner core fitted with a socket for being coupled to an external vibratory device, but the body of the tooth positioner is e.g., silicone, which fits over the hard inner core and touches every surface of the dentition, applying pressure to realign teeth as needed. Additional tooth positioners or aligners can be fabricated as treatment proceeds and the teeth progress towards optimal alignment.

Any style of tooth positioner can be used, including hinged positioners, as described in U.S. Pat. No. 4,898,535 and shown in FIG. 8A, or separate upper and lower positions, both allowing for oral access. However, since these designs require the use of vibration means for each arch, the position is preferably a unitary positioner covering upper and lower arches with holes therein for airway management can be used, as shown in FIG. 8B. The aligners or positioners can also include the force surfaces described in US20110020761, and shown in 8C. These raised areas allow the aligner to exert additional forces, thus moving difficult teeth, e.g., a force positioner can be applied to "twist" a rotated tooth into better alignment.

In other embodiments, an orthodontic remodeling device comprises a tooth positioner being U-shaped and contacting labial, lingual and occlusal surfaces of a patient's dentition; said tooth positioner shaped to apply a straightening force to at least one of said patient's teeth; said tooth positioner being operably and reversably connected to a housing enclosing a power source operably connected to a vibratory source, said vibratory source being able to vibrate at 20-40 Hz at a force of 0.1-2 Newtons and thus vibrating said tooth positioner.

The housing can be extraoral or intraoral. The tooth positioner can contact both upper and lower arches of said patients teeth, or separate upper and lower positioners can be provided for same, an upper positioner contacting an upper arch of said patients teeth, and a lower positioner contacting a lower part of said patients teeth.

The postioner can be made with various materials, and if a particularly stiff material is used, can be coated with a biocompatible resilient polymer, such as medical grade silicon. If the positioner is made of a more resilient material, it may be needed to provide a stiff inner core, at least at the socket, for adequately holding the connector or stem of the vibratory means. However, with many materials and/or smaller housings, such will not be necessary.

Although medical grade silicone rubbers are preferred for the tooth positioner since they have good tranparency, strength, no taste and a good feel, it can be made from any suitable material, including alginate, rubber, dimethylpolysiloxanes, vinyl, urethane, acrylic, polypropylenes, polyurethane, and the like. A preferred material is a low temperature vulcanizing (LTV) vinyl silicone rubber, a high temperature vulcanizing (HTV) Japanese silicone (ORTHOCON™).

While the vibrating component can be positioned intraorally, e.g., inside the tooth positioner on the inner core, an extra-oral embodiment is preferred as not being size limited and thus being able to include a processor and e.g., USB or data port to capture and transmit usage data. Clinical studies have shown that the ability to monitor usage is important to maximize patient compliance.

However, when combined with an aligner such as the Invisalign, a small intra-oral vibrator may be preferred for aesthetic reasons. Thus, each of the upper and lower aligners is fitted with one or more sockets into which a small vibrator/battery can be removably inserted, and the position of same is preferably on the lingual side where it cannot be seen. Alternatively, the vibrator can be permanently affixed thereto, or magnetically affixed with two small high field strength magnets.

The extra-oral embodiment generally includes a housing containing a vibratory source, power source and the wiring needed to operable connect and operate same. Preferably, the extra-oral embodiment also includes a processor to capture usage data and a data port or USB for communicating same, but such can be omitted, e.g., for smaller housings, especially for intraoral vibrators. The processor can also control the vibrator and in some embodiments may allow for the user to select a range of frequencies and forces, within a suitably efficacious range. The housing also includes a connector, for operably connecting to the tooth positioner, as already discussed above, and can include other components such as a charging port, or battery access hatch, indicator lights, and the like.

For patient comfort and aesthetics, the smallest and quietest means of providing vibration are employed. A large number of very small vibrating motors are available, as shown in the table below, but piezoelectric motors may be preferred due to the small size, and off-set weighted motors may be preferred due to low cost. Particularly preferred are the substantially planar motors where the vibration is substantially parallel to the substrate (e.g., U.S. Pat. No. 5,554,971, U.S. Pat. No. 5,780,958, US2009224616, US2008129130, US2007103016, WO0178217, each incorporated by reference).

| Company | Catalog | Size | Specifications |
|---|---|---|---|
| ELLIPTEC AG ™ | NA See U.S. Pat. No. 6,870,304 | 10 × 3 × 2 mm | 3-6 volts piezoelectric motor |
| SURPLUS TRADERS ™ | MF820 | 8 × 4 mm (0.315 × 0.1575 inches) | 1.5 to 4.5 VDC weighted shaft |
| SURPLUS TRADERS ™ | MF918 | 0.45 × 0.16 inches | 1 VDC to 5 VDC 18 ohms Weighted shaft |
| MOTOROLA ™ | G13566 | 0.44 × 0.18 inches | 1 VDC to 9 VDC 10 ohms Weighted shaft |
| SURPLUS TRADERS ™ | MF835 | 0.45 × 0.24 inches | 1.3 Vdc 100 mA Weighted shaft |
| MATSUSHITA ™ | V0296A | 0.24 inch diameter | 1.5 VDC Weighted shaft |
| SURPLUS TRADERS ™ | ME235 | 0.24 × 0.5 inches | 1.5 to 3 VDC 62 mA weighted shaft |
| PRECISION MICRO-DRIVES ™ | 304-002 | 4 mm × 8 mm | 2.3 VDC to 3.6 VDC 100-120 mA 11000 rpm Weighted shaft |
| PRECISION MICRO-DRIVES ™ | 308-100 | 3.4 × 8 | 2 to 3.3 V, 120 mA 12000 rpm 8 mm Shaftless Vibration Motor |

In addition to electromagnetic motors and piezoelectric motors, other motor types could be used including mechanical actuators, ultrasonic motors and the like. Vibrations may be oscillating, random, directional, circular, and the like. Vibrators are well within the skill of the art, and several are described in the patent literature (and commercially available as seen above). For example, US2007299372, US2007255188, US2007208284, US2007179414, US2007161931, US2007161461, US2006287620, each incorporated by reference, describes various vibrator motors.

The cyclic forces or vibration applied to the tooth positioner is at frequencies between 1 to 1000 Hz or 1-1200 Hz (preferably 10-100 Hz and most preferred 20-40 or 30 Hz) and a force of 0.01-5 Newtons (or 0.1-0.5 or 0.2-0.3 or 0.25 Newtons) for a period of 1-60 minutes, preferably about 1-30 or 1-10 minutes or 20 minutes. This is followed by a period of recovery, ranging from 2-24 hours, preferably from 4-12 hours, and the cycle is repeated until one or more teeth are successfully moved.

More particularly, the orthodontic appliance of the invention has a vibrational source capable of providing a vibratory force at a frequency of about 30 Hz and a force of about 0.25 Newtons. Excess force is generally unpleasant to the patient, especially force coupled with high frequency, and in preferred embodiments these parameters are patient adjustable within clinically efficacious ranges. The force can be changed to accommodate different materials, usually being reduced with stiffer materials and increased with softer materials.

In addition to capturing and storing usage data, the processor can also control the force and frequency parameters, and appropriate controls or user interface can be provided form same.

Preferably, the vibrating component has a more stable vibrator with improved performance characteristics of decreased sound and low variance frequency and force. In particular, the improved vibrator has a noise level less than 55 dB when measured at 6 inches, a frequency at 20-40 Hz, with a variance of only 2 Hz, and a force of 0.1-0.5 Newtons, with a variance of +−0.05 N.

Consistency of frequency and force is achieved e.g., via a feedback loop whereby motor speed is monitored and software adjusts the motor as needed. More particularly, the motor contains an integrated encoder that provides multiple high and low signal outputs per every motor revolution. The software counts the time between every encoder event and compares this to the desired target (e.g., 30 Hz). Based on this comparison, the software then adjusts the pulse width modulation that is driving the motor to increase or decrease speed as appropriate to maintain the desired speed. Accurate controlling of speed also controls the force.

A DC 6V Motor having off-set weight and 8 line integrated encoder is known to provide these characteristics, but other vibrators may also provide these performance characteristics, and can be easily tested for same. Preferably the battery is a chargeable 100 mAh Li battery. Preferably, the motor is the Series 1506 DC Motor, by Micromo Electronics, Inc. (Part No. 1506N006SRIE2-8), and the battery is a 100 mAh Li—PO battery by Harding Energy (Part no. BAN-E601421).

Batteries may drive the vibrational source for some intra-oral embodiments. Small coin batteries, alkaline or lithium, are preferred due to their small size, but hydrogen batteries may also be preferred due to their power and power density, particularly as size and cost decrease with further technological development. At this time, rechargeable batteries are preferred, and thus the housing can also contain an access port or charging port for same.

For certain embodiments, a battery that can be wirelessly recharged is preferred for longer product life (e.g., US2009051312, U.S. Pat. No. 7,511,454), but in other embodiments a low cost device is manufactured that is intended to be disposable. It is known in the art to select an appropriate power source/motor combination to provide a complementary orthodontic force that vibrates within the frequency and power suitable for orthodontic remodeling.

Another improvement on the extra-oral vibrating device is the provision of a separate charging stand that serves to dock the vibrator and charge it at the same time. The charging station also has a display and software so that the user can see the usage data. Thus, a dental professional (or parent) can determine whether the patient is using the device as intended. In one embodiment, the display shows the number of uses per running 7 days (for example 6/7=86%), the number of uses per running 30 days (25/30=83%)) and the total number of uses (145 uses). A USB port can provide the same functionality.

Any off the shelf on/off switches can be used. Particularly preferred for the intraoral device is an on/off switch with depressible activator (push button or rocker). However, for the extra-oral vibratory device any off/on switch or rotating dial can be used.

The device of the invention can be used in a variety of oral and maxillofacial applications including malocclusion, trauma repair, temporomandibular joint and muscle disorders (TMJDs), Lefort and other skeletal facial fractures, craniofacial anomalies such as boney clefts, bone defects, dentofacial deformities, dental implants, periodontal bone grafts as well as tooth, muscle, nerve, tendon, ligament, bone, and connective tissue repair.

As used herein, "tooth positioner" means a custom made intra-oral bite plate that contacts occlusal, facial and lingual surfaces of the teeth, preferably both arches with a single bite plate, but wherein the imprint for one or more teeth has been adjusted in position, so as apply a corrective pressure to one or more teeth and allowing orthodontic correction. The term is intended to include tooth positioners used only for finishing, as well a total treatment aligners, and such. It does not include traditional archwire and brace orthodontics.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

| ABBREVIATION | EXPANSION |
| --- | --- |
| LTV | low temperature vulcanizing |
| HTV | high temperature vulcanizing |

BRIEF DESCRIPTION OF THE DRAWINGS

A more complete understanding of the present invention and benefits thereof may be acquired by referring to the following description taken in conjunction with the accompanying drawings in which:

FIG. 8A-C show prior art positioner styles, including a hinged positioner in FIG. 8A, and a traditional positioner with holes for airway management in FIG. 8B.

DETAILED DESCRIPTION

Turning now to the detailed description of the disclosure, the figures are described in some additional detail.

Figure 1A:
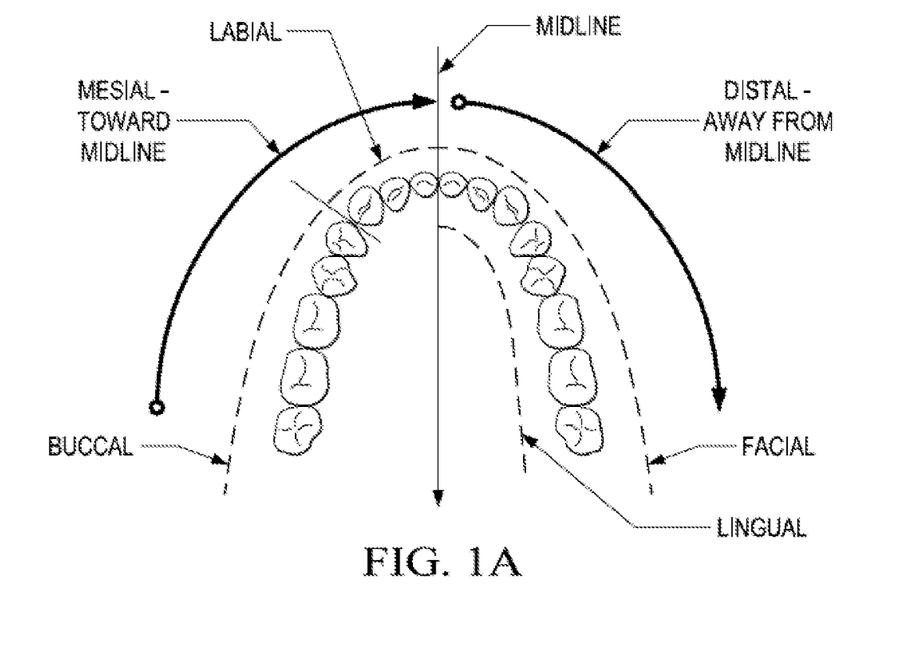
FIGS. 1A and 1B provide standard dental nomenclature for the dentition surfaces.
Figure 1B:
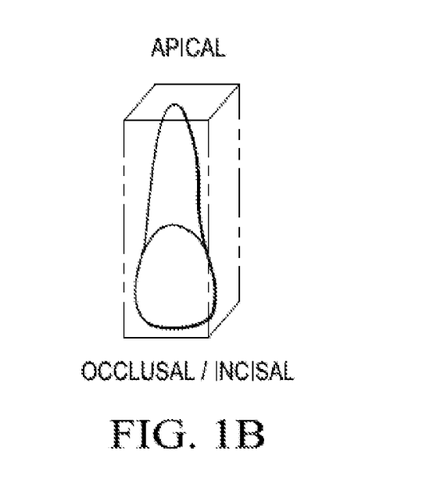

FIG. 1 shows the various surfaces of the teeth, and is helpful for orienting the reader to standard dental terminology. The facial, lingual and occlusal surfaces of the teeth are shown, and the tooth positioner is designed to contact all of these surfaces and apply a corrective pressure to one or more teeth. The names of individual teeth are omitted from this figure, but are standard in the art.

Figure 2:
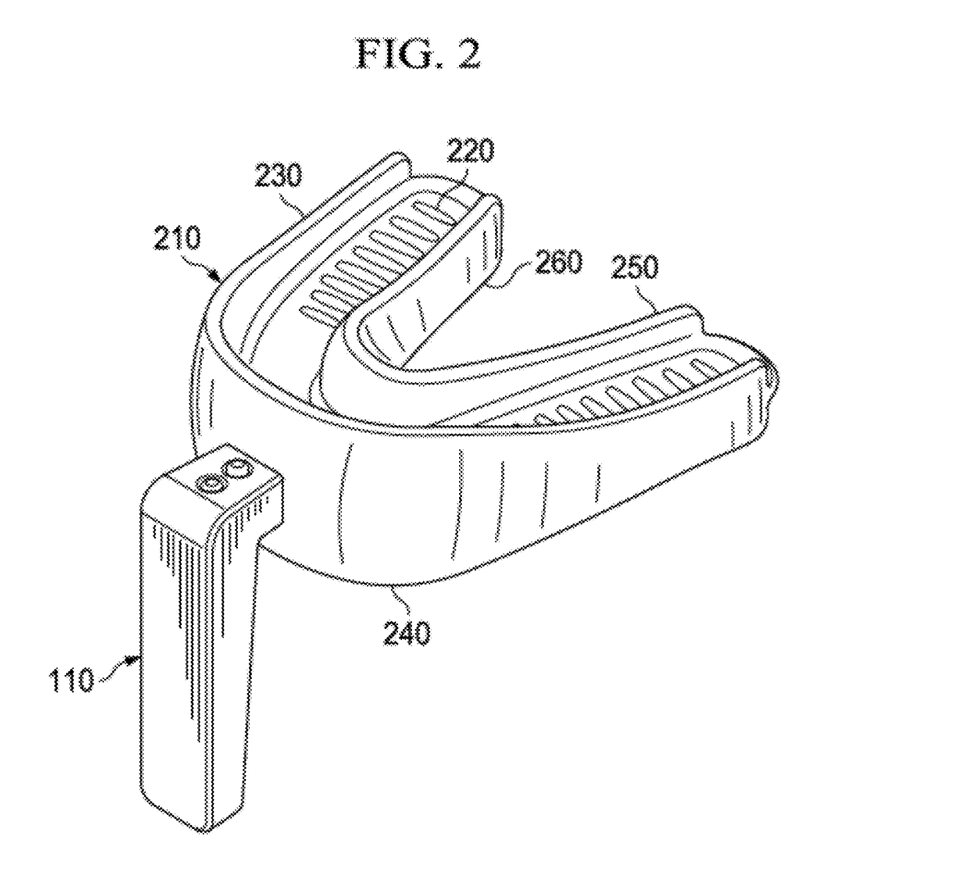
FIG. 2 is a perspective view of the extra-oral vibratory device and tooth positioner.
Figure 3A:
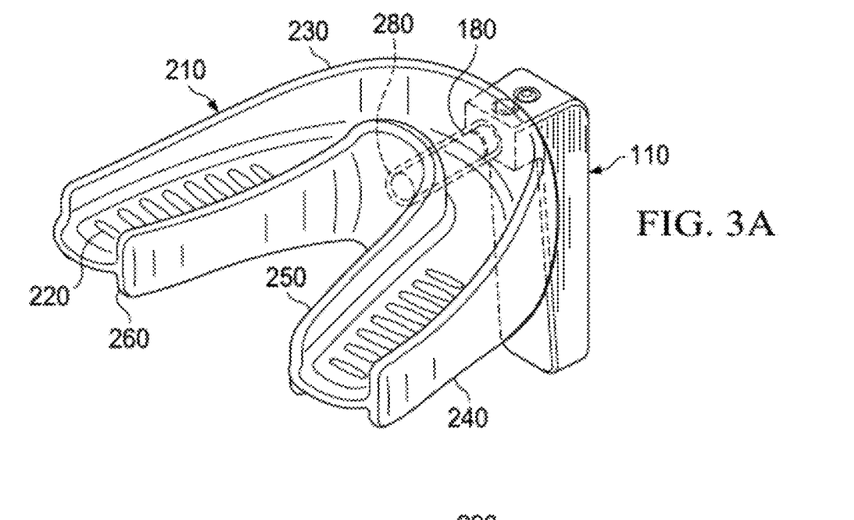
FIGS. 3A and B include two transparent perspective views from opposite angles of the tooth positioner with socket.
Figure 3B:
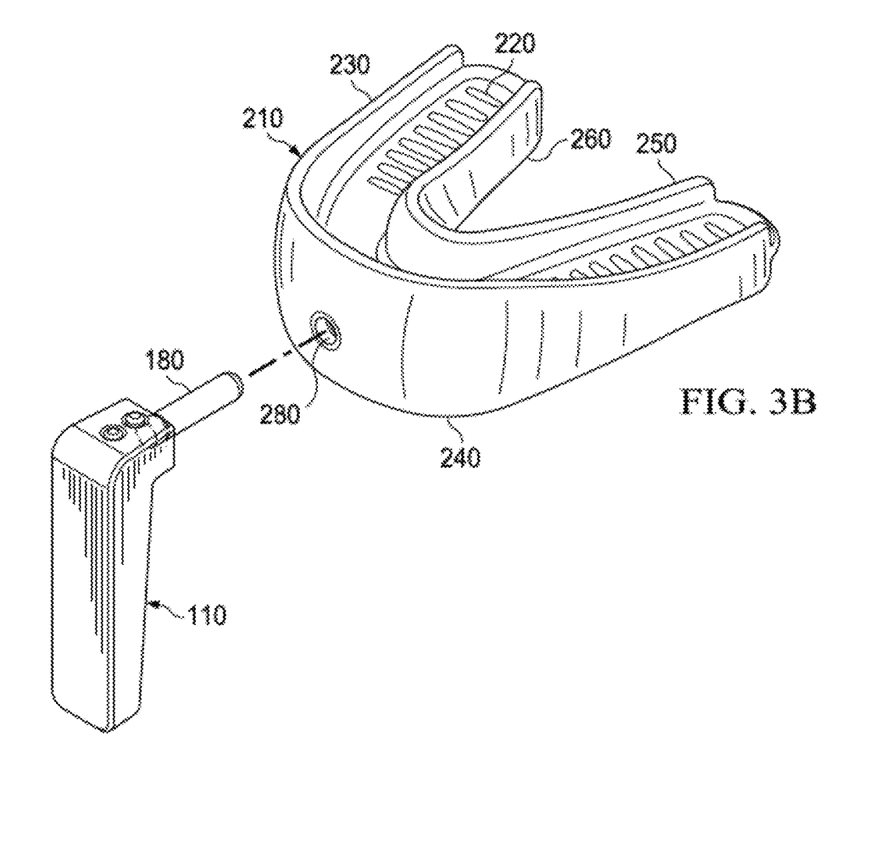

FIG. 2 shows a perspective view of the extra-oral vibratory device 110 with tooth positioner 210. FIGS. 3A and 3B more clearly illustrates the tooth positioner from two different angles. It is generally U-shaped, as is the dentition, and has a flat surface 220 that contacts the occlusal surfaces of the teeth. Here, the tongue area is shown empty, but this is not essential, and the central portion of the U-shape can also be filled in, provided the overall form is still comfortable. The generally flat surface 220 also has labial/buccal (aka facial) and lingual edges on both the upper and lower sides, which contact the labial and lingual surfaces of the upper and lower dentition. More specifically, 230 is the upper labial edge, 240 is the lower labial edge, 250 is upper lingual edge and 260 is lower lingual edge. Also shown is socket 280 into which a complementary stem 180 fits.

Figure 5:
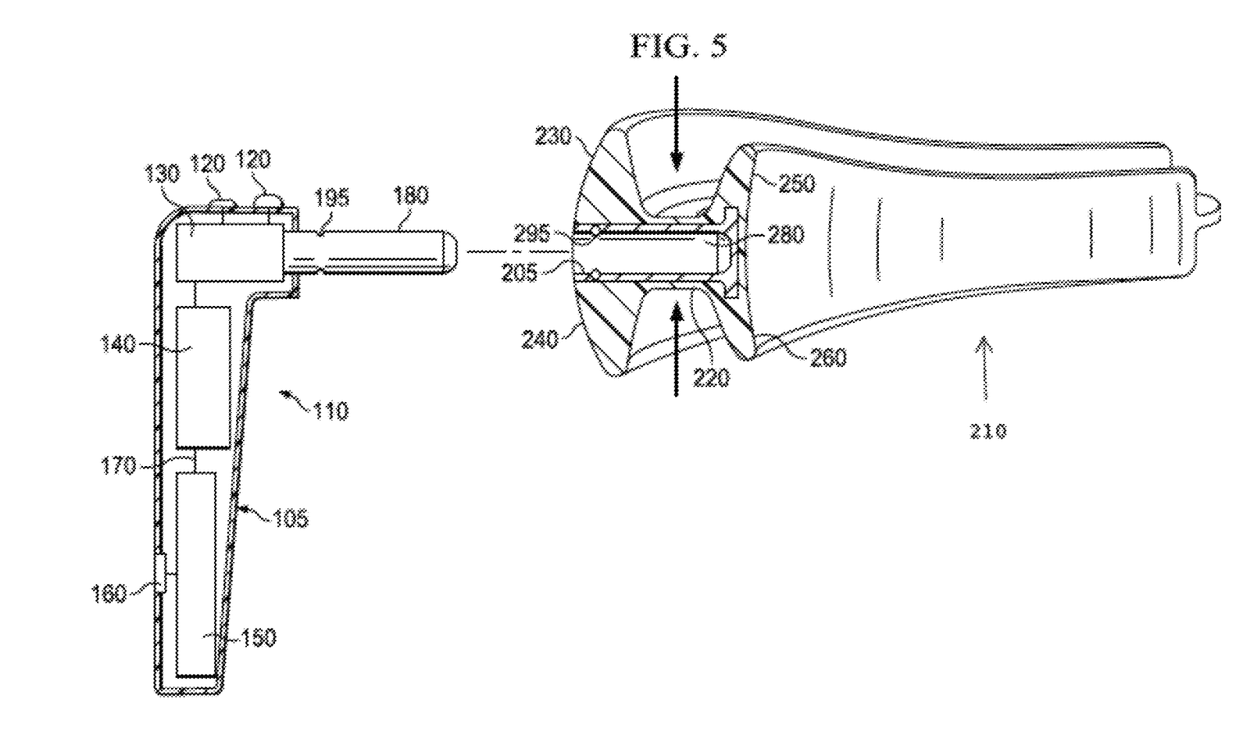
FIG. 5 shows a cross-sectional view of a half of a tooth positioner, illustrating an exemplary socket with a different snap fit.
Figure 6:
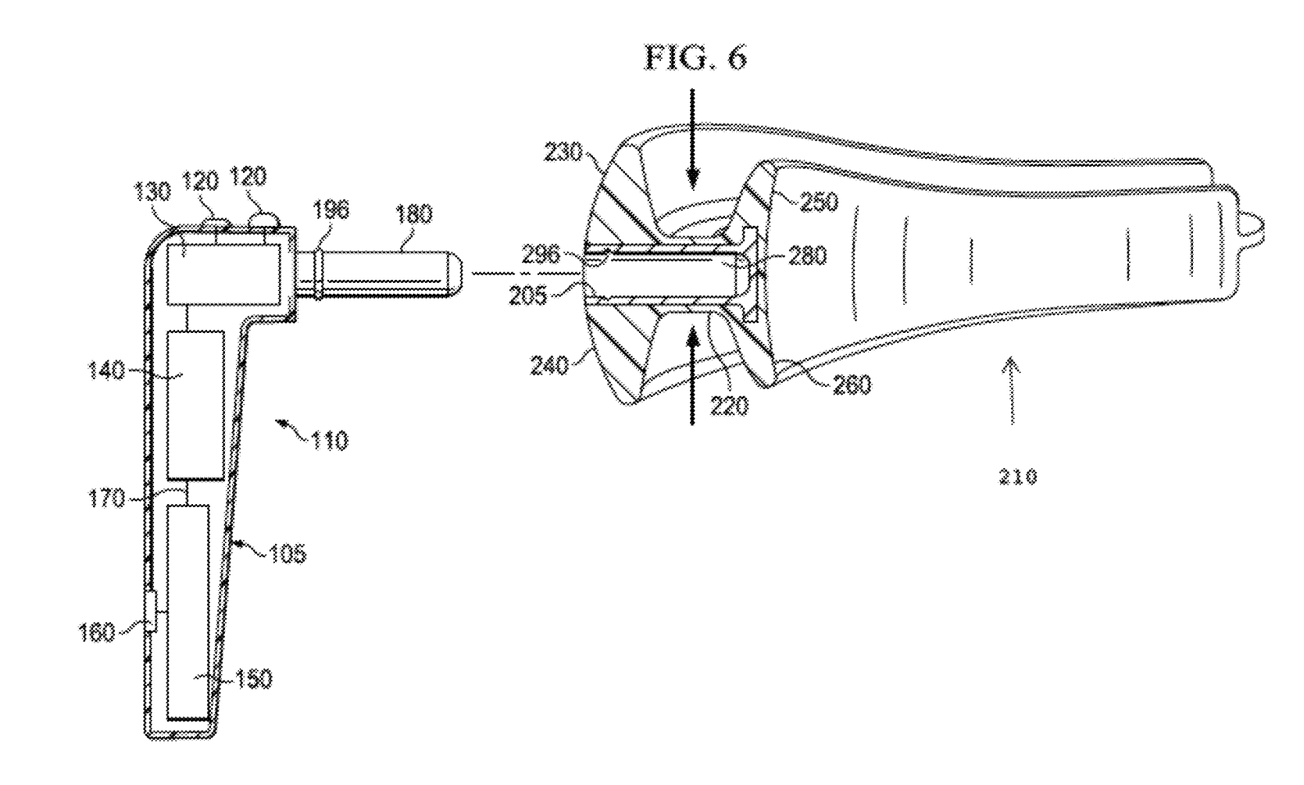
FIG. 6 shows a cross-sectional view of a half of a tooth positioner, illustrating an exemplary socket with a different snap fit.
Figure 7A:
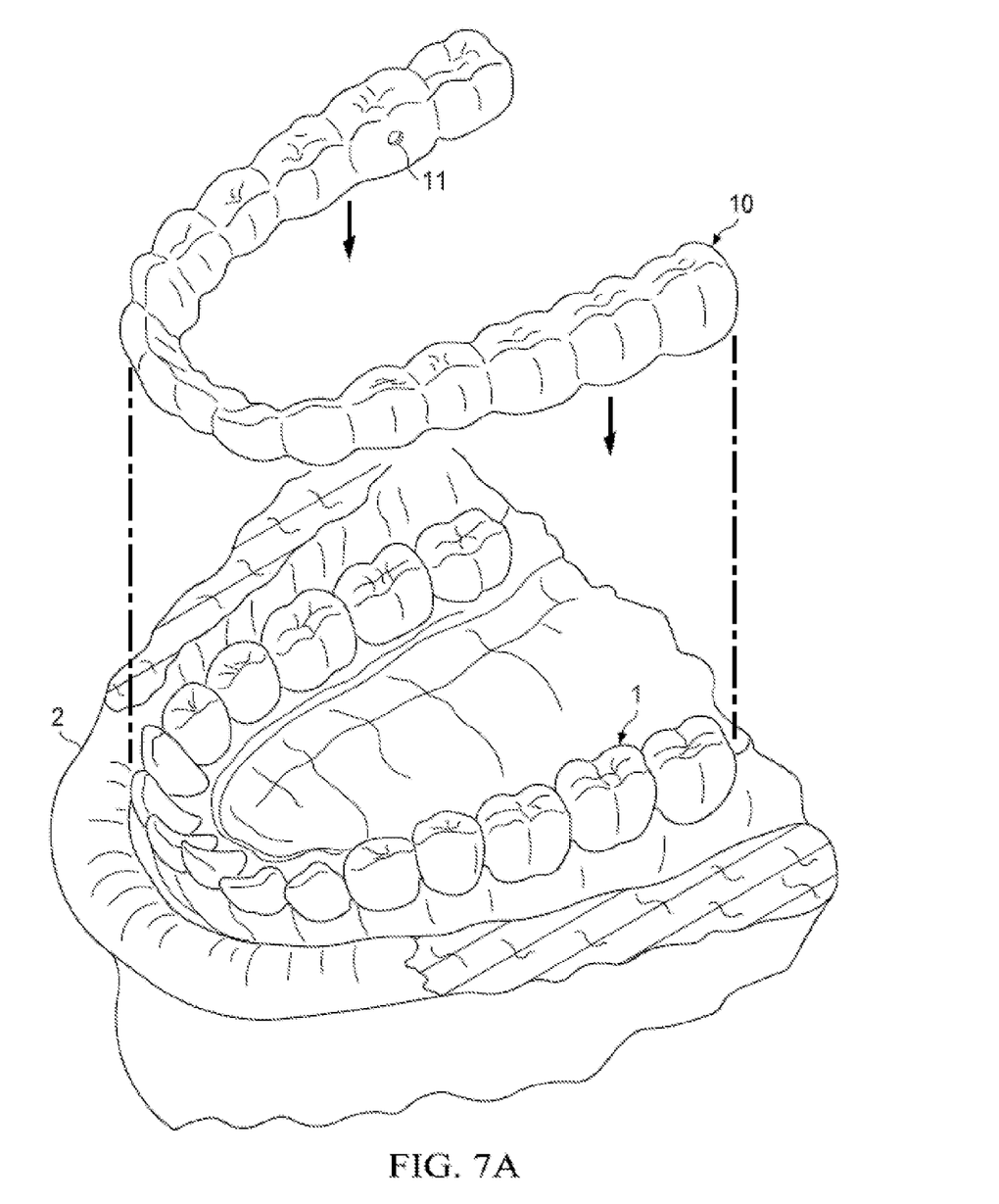
FIG. 7A shows an aligner and teeth.

Note that the surfaces 220, 230, 240, 250, 260 are shown quite simply in FIG. 2-6, but in fact these surfaces will closely mimic tooth shape, but with at least one area modified to apply a realignment pressure to that area. However, straight surfaces are shown for ease of illustration and understanding. FIG. 7 shows an aligner where the tooth shape is closely mimicked, and the bite plates of FIG. 2-6 will have a similar internal shape, and may also have a similar external shape for aesthetic and comfort reasons.

FIG. 2 shows an extraoral housing, but if the electronics are simplified and/or miniaturized it would be possible to but the vibrator on the inside of the device, e.g., lingually, and such may be preferred as it would minimize droolling, which tends to occur if the lips are held open, e.g., by an extraoral housing.

Figure 4:
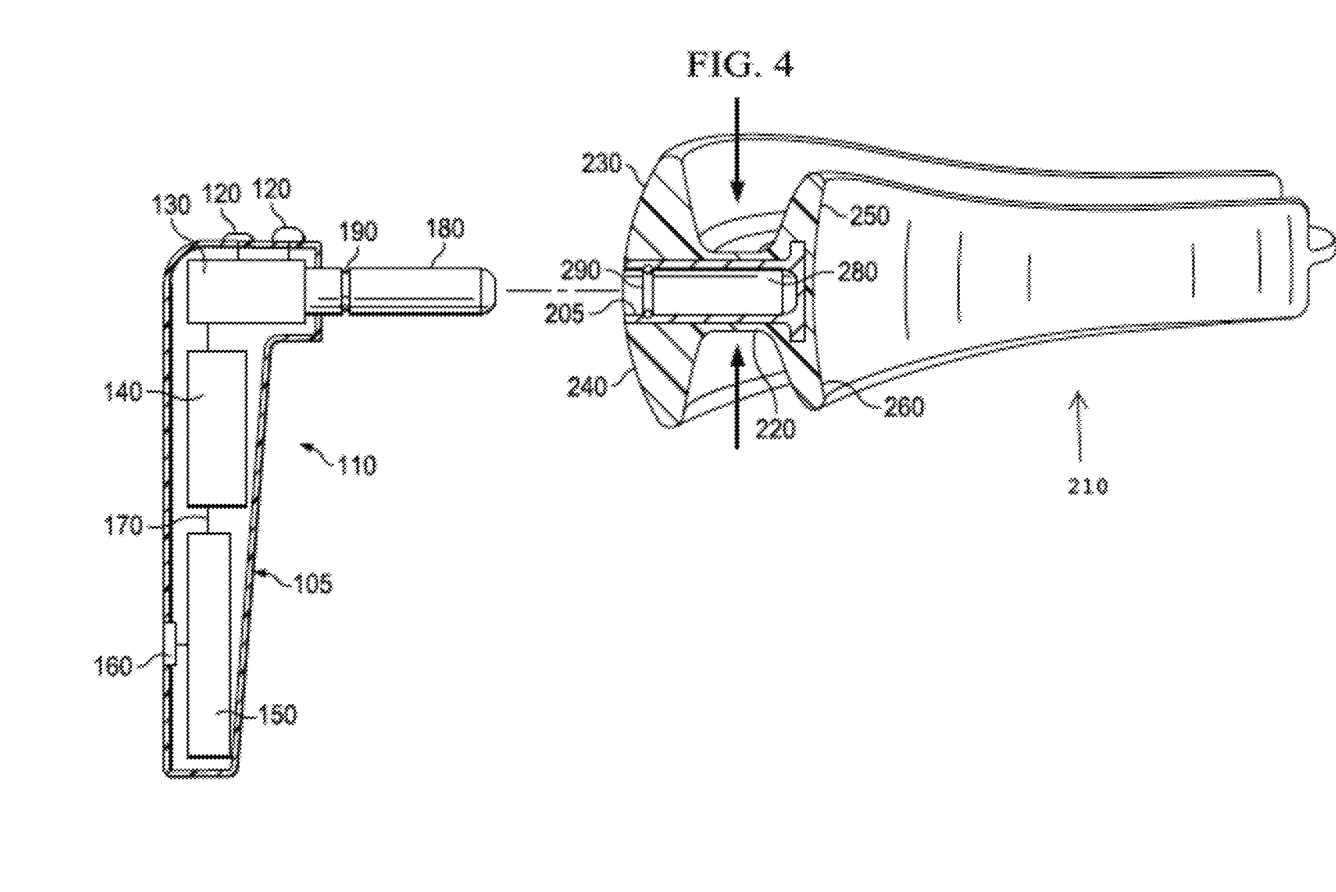
FIG. 4 is a cross-sectional view of a half of a tooth positioner, illustrating an exemplary socket in further detail. Also shown is a schematic of the extraoral vibrator with stem that fits into the socket.

Another exemplary structure is illustrated in FIG. 4, which is a cross section of the vibratory device 110 and half of a tooth positioner 210. The vibratory device 110 has a housing 105 containing all components, except the stem 180, which protrudes therefrom. Preferably, housing 105 is water resistant or even more preferred it is waterproof or hermetically sealed. The housing contains battery 130, preferably a rechargeable battery and can have an optional charging port (not shown). A source of vibration 140, which is preferably an offset motor or piezoelectric motor is shown schematically as a simple box. Processor 150 controls the vibratory source 140, and may also capture and store compliance data. Data is transmitted to a server or computer or the internet via data port or USB 160. Connections or wires 170 are shown in simple form only and not intended to convey actual wiring connections, as are on/off switches 120. Stem 180 is shown here with depressions 190, which can circumnavigate the stem in one embodiment, but many variations of snap fitting and other connectors are possible. For example, cantilevered snap fits, cyclindical snap fits, and ball (spherical) snap fits are all possible, and can be combined with buttons for a reversable coupling, or not, depending of the degree of material stiffness, coefficient of friction and lead and return angles.

Tooth positioner 210 can have a hard inner core that forms the socket 205 and can be any suitable shape. A circle spring 290 fits into depressions 190 on stem 180 and the tooth positioner thus removably snap fits onto the extraoral vibratory device. The tooth positioner has the labial, lingual edges and occlusal surface as already described in FIG. 3. Thus 220 is the flat surface which contacts occlusal surface of the teeth, edges 230 and 240 contact the facial tooth surfaces, while edges 250 and 260 contact the lingual tooth surfaces. These various surfaces, 220, 230, 240, 250 and 260 are shaped to closely follow a patient's teeth, but with adjustments made to pressure poorly aligned teeth into a more desirable position. Preferably, these edges are made of or at least coated with a resilient material of durometer at least 70 Shore A, most preferred is a biocompatible or medical grade clear silicone.

Similar devices are shown in FIG. 5, but in FIG. 5 stem 180 is fitted with the holes 195 into which spring pins 295 fit. In FIG. 6, stem 180 has a ridge or protrusion 196 that circumnavigates stem 180, and which fits into a corresponding depression 296 in socket 205.

Figure 7B:
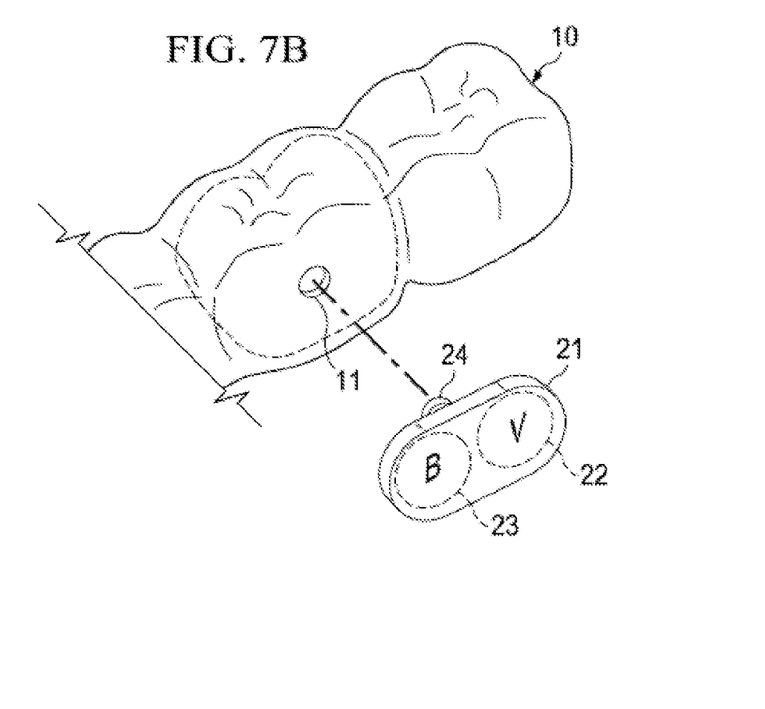
FIG. 7B shows a close up of one tooth having a socket into which a vibrator can fit (vibrator not drawn to scale).
Figure 7C:
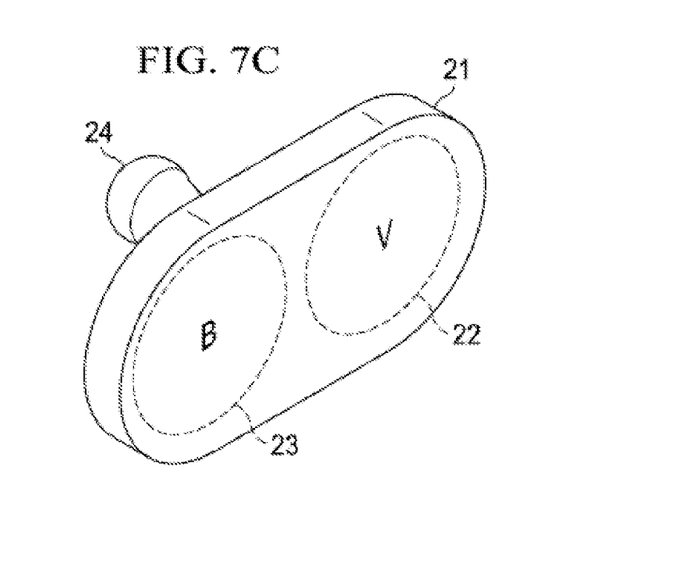
FIG. 7C shows a close up of a vibrator with stem.

FIG. 7 shows an aligner combined with a vibrator. Only the lower jaw and lower teeth 1 are shown, above which is an transparent aligner 10. An upper aligner is not shown herein, but usually the aligners are custom made for both upper and lower jaw. Aligner 10 is adapted to have a small socket 11 into which the removable vibrator can be fit. The removable vibratory device has a housing 21 enclosing a vibrator 22 and battery 23. In this instance, due to size limitations, a peizeolectric vibrator 22 may be preferred, together with a small coin battery 23.

Of course the socket and stem can be reversed, the aligner having a stem, and the vibrator having a socket. Such may be preferred for very thin aligners, which may not allow entry of a stem without applying pressure to the teeth. Alternatively, the socket can be built up from the surface of the aligner, thus not impinging the teeth. As yet another alternative, such attachment means can be eliminated and replaced e.g., with adhesive or a magnetic mounting means.

We show herein a small vibratory device, but the vibratory device can also mirror the shape of the aligner, fitting against the lingual surface, optionally have more than one vibrator therein, and still snap fit into at least two sockets. It is also possible to permanently affix a vibrating component to the inner surface of the aligner, since aligners are used for only a limited time, and then a new aligner is provided. Thus, it is possible to make a low profile, watertight vibrator with sufficient battery life to last the life of the retainer that is affixed to the aligner with snap fit mating parts or adhesives or other methods. A patient accessible on/off switch will be required, e.g., a low profile depressible button, when the vibrating component is not removable.

Housing 21 is watertight (hermetically sealed), such that the components therein do not get wet, and also has a smoothly curved, low profile so as to not overly interfere with tongue placement, and such. The housing may also have a stem 24 projecting from it, that snap fits into hole 11. In preferred embodiments, the stem can also function as a depressible on/off switch, such that inserting the device into hole 11 simultaneously activates it, causing it to vibrate. If desired for cost reasons, the processor can be omitted, and the vibrating component inexpensively made such as to be disposable when the battery wears out. In other embodiments, the housing can have an access hatch for replacing the battery.

The placement of hole or socket 11 can vary on the aligner 10, but is shown adjacent wisdom teeth here on the lingual side, although it can also be placed on the facial side if the profile of the vibratory component is sufficiently flat and the socket 11 back far enough (e.g., positioned buccally and hidden by the cheek) so as the vibratory component is not visible when the patient smiles. Hole 11 can be accompanied by a matching hole on the other side. Alternatively, hole 11 could also be placed near lip 2, but on the lingual side of the aligner so as to not mar the aesthetics of the aligner.

Figure 8A:
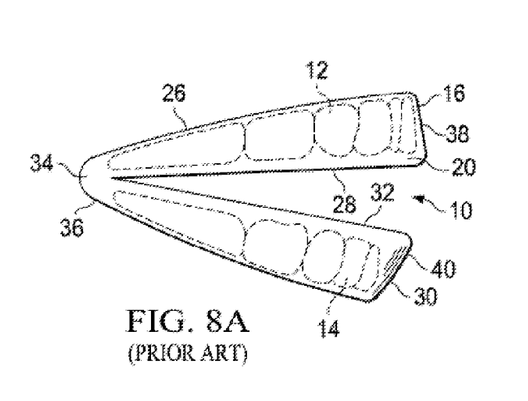
Figure 8B:
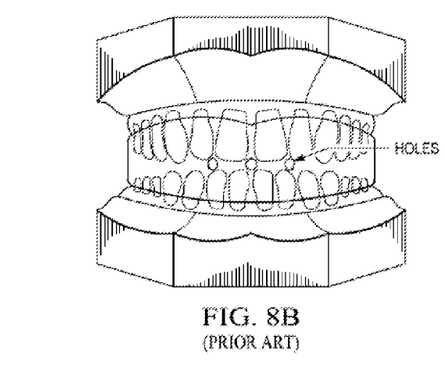
Figure 8C:
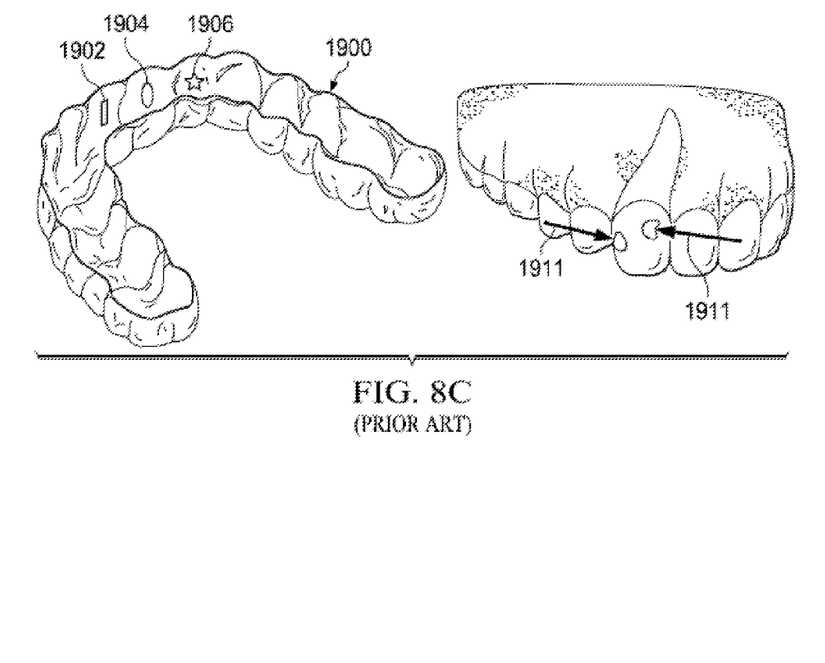
FIG. 8C is an aligner with pressure pockets and corresponding raised surfaces that are adhered to teeth. Any of these positioner styles can be combined with vibratory means, as described herein.

FIG. 8A shows the hinged positioner of U.S. Pat. No. 4,898,535, wherein positioner 10 includes an upper trough 12 for receiving the maxillary or upper row of teeth, and a lower trough 14 for receiving the mandibular or lower row of teeth. The troughs are formed generally by a labial-buccal flange 16 and a lingual flange 18. The flanges are connected by an isthmus portion 20. Both the upper and lower troughs are provided with tooth receiving depressions or sockets 22, 24. A connecting hinge portion 34 is formed at a posterior end 36 of the appliance since the bite plate is slit only partially through the appliance thus leaving an anterior end 38 of the upper part 26 and an anterior end 40 of the lower part 30 separate from each other.

FIG. 8B shows a typical positioner contacting both upper and lower arches, with three holes (arrow) shown for airway management. Such a positioner can easily be modified to accept one or more stems in these holes, and if needed the holes lined with a stiffer material than the rest of the positioner. Additional airway management perforations can be provided if desired.

An aligner with pressure pockets, as described in US20110020761 is shown in FIG. 8C. The appliance 1900 is provided with one or more depressions 1902, 1904, 1906, which can be any shape, and function to allow force to be applied to corresponding raised surfaces that are adhered to teeth (see arrows). These raised areas allow the aligner to exert additional forces at various angles depending on the position/shape of the raised area. The raised pressure buttons 1911 fit into the pockets 1902, 1904, 1906, and allow the moving of difficult teeth, e.g., a force positioner can be applied to "twist" a rotated tooth into better alignment.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

Each of the following patents is incorporated by reference in its entirety.

US2006223022
US2006287620
US2007103016
US2007161461
US2007161931
US2007179414
US2007208284

US2007255188
US2007299372
US2008129130
US2008227046
US2009051312
US2009068612
US2009224616
US2010055634
US2010055634
US2011236849
US2011039223
US20110020761
U.S. Pat. No. 3,407,500
U.S. Pat. No. 4,244,688
U.S. Pat. No. 4,348,177
U.S. Pat. No. 4,348,178
U.S. Pat. No. 4,382,780
U.S. Pat. No. 4,898,535
U.S. Pat. No. 5,030,098
U.S. Pat. No. 5,554,971
U.S. Pat. No. 5,780,958
U.S. Pat. No. 5,967,784
U.S. Pat. No. 6,632,088
U.S. Pat. No. 6,684,639, U.S. Pat. No. 6,832,912, U.S. Pat. No. 7,029,276
U.S. Pat. No. 7,511,454
WO0178217
WO2007116654

The invention claimed is:

1. An orthodontic remodeling device comprising:
an extra-oral vibrator comprising a waterproof housing containing a power source operably coupled to a vibrator operably coupled to a processor for controlling said vibrator and for storing compliance usage data operably coupled to a data port for transmitting said data;
said housing also having a connector protruding therefrom;
a tooth positioner shaped to closely fit a patient's dentition and apply a straightening force to at least one of said patient's teeth, said tooth positioner being made of a resilient material that contacts labial, lingual and occlusal surfaces of said patients dentition, and having an inner rigid core shaped to accept said connector, such that said tooth positioner can be operably and removably coupled to said extra-oral vibrator,
said vibrator being able to vibrate at 1-1200 Hz at a force of 0.1-5 Newtons and thus vibrating said tooth positioner when coupled to said extra-oral vibrator.

2. The orthodontic remodeling device of claim 1, said vibrator being able to vibrate at 10-40 Hz.

3. The orthodontic remodeling device of claim 1, said vibrator being able to vibrate at a force between 0.1-0.5 Newtons.

4. The orthodontic remodeling device of claim 1, wherein said power source is a rechargeable battery.

5. The orthodontic remodeling device of claim 1, wherein said power source is a rechargeable battery and said housing includes a charging port.

6. The orthodontic remodeling device of claim 1, wherein said inner rigid core is metal.

7. The orthodontic remodeling device of claim 1, wherein said inner rigid core is a plastic of less than 40 Shore D.

8. The orthodontic remodeling device of claim 1, wherein said resilient material is medical grade silicone.

9. The orthodontic remodeling device of claim 1, wherein said inner rigid core is a plastic of less than 40 Shore D and said resilient material is medical grade heat cured silicone subber.

10. The orthodontic remodeling device of claim 1, wherein said inner rigid core is a metal and said resilient material is medical grade silicone.

11. The orthodontic remodeling device of claim 1, said device having a noise level less than 55 dB when measured at 6 inches, and being capable of vibrating at a frequency between 20-40 Hz with a variance of only 2 Hz, and a force between 0.1-0.5 Newtons with a variance of +−0.05 N.

12. The orthodontic remodeling device of claim 11, said vibrator being an offset motor with an 8 line integrated encoder.

13. The orthodontic remodeling device of claim 11, said vibratory source being a DC 6V motor having off-set weight and 8 line integrated encoder.

14. The orthodontic remodeling device of claim 1, said device having a noise level less than 55 dB when measured at 6 inches, and being capable of vibrating at a frequency between 20-40 Hz with a variance of only 2 Hz, and a force between 0.1-0.5 Newtons with a variance of +−0.05 N, wherein said inner rigid core is a plastic of less than 40 Shore D and said resilient material is medical grade silicone.

15. The orthodontic remodeling device of claim 1, said device having a noise level less than 55 dB when measured at 6 inches, and being capable of vibrating at a frequency of 20-40 Hz, with a variance of only 2 Hz, and a force of 0.1-0.5 Newtons, with a variance of +−0.05 N, wherein said inner rigid core is metal and said resilient material is medical grade silicone.

16. A method of orthodontic remodeling comprising using the device of claim 1 in a vibrating mode for at least 10 minutes a day.

17. A method of orthodontic remodeling comprising using the device of claim 1 in a vibrating mode for at least 10 minutes a day and using the tooth positioner alone in a non-vibrating mode at least overnight.

* * * * *